United States Patent [19]

Madgavkar et al.

[11] 4,263,467

[45] Apr. 21, 1981

[54] RECOVERY OF BORON TRIFLUORIDE FROM A HYDROCARBON LIQUID

[75] Inventors: Ajay M. Madgavkar, Pittsburgh; Robert Bartek, Windber, both of Pa.

[73] Assignee: Gulf Research & Development Company, Pittsburgh, Pa.

[21] Appl. No.: 98,499

[22] Filed: Nov. 29, 1979

[51] Int. Cl.$^3$ ............... C07C 2/08; C07C 7/12; C01B 35/06; B01J 19/04
[52] U.S. Cl. ............... 585/525; 23/293 R; 55/36; 55/52; 55/71; 423/293; 585/800
[58] Field of Search ............ 23/293 R; 585/525, 800; 423/293; 159/5, DIG. 29, 49; 55/36, 52, 71, 68; 203/89, 91

[56] References Cited

U.S. PATENT DOCUMENTS

| | | |
|---|---|---|
| 2,284,554 | 5/1942 | Beyerstedt .................. 423/293 X |
| 2,528,982 | 11/1950 | Lien et al. ..................... 585/800 |
| 2,764,533 | 9/1956 | Oetjen et al. ................. 55/52 X |
| 2,997,371 | 8/1961 | Wadsworth et al. .......... 423/293 |
| 3,377,778 | 4/1968 | Gaertner ........................ 55/52 |

*Primary Examiner*—Joseph Scovronek

[57] ABSTRACT

A method for recovering dissolved boron trifluoride from a hydrocarbon liquid in a vacuum column at moderate temperatures by trickling the hydrocarbon over metallic or ceramic packing in the column. Dissolved boron trifluoride catalyst is recovered from the crude oligomer reaction product resulting from the oligomerization of 1-decene.

6 Claims, No Drawings

RECOVERY OF BORON TRIFLUORIDE FROM A HYDROCARBON LIQUID

SUMMARY OF THE INVENTION

In its broadest aspect this invention relates to the recovery of boron trifluoride which is dissolved in a liquid hydrocarbon. The recovery is effected by flowing the hydrocarbon liquid downwardly through a column under reduced pressure and at a moderate temperature such as room temperature over the surface of pelleted or shaped packing material to desorb and vaporize the boron trifluoride from the liquid hydrocarbon. This invention is particularly suited for the recovery of boron trifluoride catalyst which is dissolved in the crude oligomer product mixture obtained by the oligomerization of a 1-olefin such as 1-decene.

DESCRIPTION OF THE INVENTION

Synthetic lubricants and other functional fluids have been prepared by the oligomerization of 1-olefins such as 1-decene using boron trifluoride complexed with a polar compound such as n-butanol. Since these catalyst complexes, if recovered, cannot be reused because of a substantial decrease in activity, this oligomerization process involves the continuing expense of fresh catalyst and the concomitant costly waste treatment and disposal procedures which are necessary to prevent environmental contamination from the discarded catalyst.

If the oligomerization reaction is carried out by contacting the 1-olefin containing dissolved boron trifluoride with a solid adsorbent material such as particulate silica, the dissolved boron trifluoride can be recovered from the liquid product mixture for reuse. For example, the product mixture can be heated to a suitable temperature such as 100° C. and nitrogen gas can be bubbled through the liquid mixture to effectively sweep out the boron trifluoride. However, the boron trifluoride gas must then be separated from the nitrogen gas. A vacuum can be used in substitution of the nitrogen sweep at 100° C. for effective boron trifluoride removal. However, both procedures involve the heating of the reaction mixture containing the dissolved boron trifluoride catalyst to a temperature which is substantially higher than the oligomerization temperature thereby subjecting the components of the crude reaction mixture to further undesired reaction.

We have discovered that the dissolved boron trifluoride can be removed from this crude oligomer product mixture in a process which functions at the temperature of the oligomerization process and therefore does not require the heating of the crude product mixture while it contains the dissolved boron trifluoride. In our process the crude oligomer product is removed from the oligomerization reactor and is directly introduced into a non-heated boron trifluoride recovery column which is operated at reduced pressure. Since the boron trifluoride recovery can be effectively carried out at room or ambient temperatures (about 20° to 25° C.), the crude oligomer product or other hydrocarbon liquid which contains dissolved boron trifluoride can also be stored at room temperature and subsequently treated by our recovery process at a future convenient time without heating the liquid.

In order to assist in the vaporization of the boron trifluoride at ambient or equivalent temperatures, the boron trifluoride recovery column contains a metallic or ceramic packing material. The hydrocarbon liquid is introduced into the upper portion of the column above the packing and is permitted to trickle downwardly over the wetted surfaces of the packing material. Since the interstice between the packing material in this trickle technique is a vapor phase, the surfaces of the packing material are coated with a relatively thin layer of the descending liquid such that there is no portion of the descending liquid as well as the dissolved boron trifluoride, which is not physically proximate to the vapor phase in the column. As a result of this procedure, the dissolved boron trifluoride is substantially removed from the crude reaction liquid. This boron trifluoride is recovered in its pure state and is therefore reusable in the process as it is recovered without change from its original activity.

This boron trifluoride recovery procedure is desirably operated within a broad temperature range of between about −30° and about 50° C. and preferably between about −10° and about 30° C. In order to obtain a suitable rate of desorption of the boron trifluoride from the reaction liquid, the recovery column is operated under a maximum pressure of about 600 millimeters of mercury absolute, preferably a maximum pressure of about 300 mm. of Hg.

The column packing which is useful herein for removing the dissolved boron trifluoride by the trickle technique is not critical. Any conventional metallic or ceramic packing material such as that used in distillation or absorption columns can be used. It can be spherical, rod, ring, tubular, saddle or irregularly shaped. We prefer to use packing material which provides a high surface area per unit volume. In general, this packing material will be between about 1 and about 50 mm. in maximum dimension and preferably between about 3 and about 20 mm. in maximum dimension.

In our recovery process the crude oligomer reaction product or other liquid hydrocarbon containing dissolved boron trifluoride is introduced into the boron trifluoride recovery column as it comes from the reactor. The rate that the liquid is fed to the column is not critical except that the longer the liquid remains in the column, other conditions remaining the same, the greater the recovery of boron trifluoride. With this in mind, we prefer to operate at a liquid hourly space velocity (LHSV hr.$^{-1}$) of 0.1 to 5, most preferably 0.2 to 2 volumes of liquid per volume of catalyst per hour. This liquid reaction product trickles down the column over the surfaces of the packing material. As the boron trifluoride vaporizes out of the reaction liquid into the vapor phase, it is withdrawn from the recovery column through the vacuum line and is directed to a boron trifluoride storage container ready for use in the oligomerization or other reaction.

After passing through the packing, the liquid reaction product is removed from the bottom of the recovery column. It is then washed with water, preferably containing base, such as sodium hydroxide, to remove any trace amounts of boron trifluoride remaining in the product liquid. Since this trace boron trifluoride is only a minute portion of the boron trifluoride that is fed to the reactor, make-up catalyst costs and catalyst disposal costs are minimized and the environmental problems involving catalyst disposal are substantially eliminated by the present process.

DESCRIPTION OF PREFERRED EMBODIMENTS

EXAMPLE 1

The oligomerization of 1-decene was carried out in a vertically mounted, stainless steel reactor one-half inch (12.7 mm.) in internal diameter and two feet (61 cm.) in length and containing 30 cc. of 10/20 mesh (0.8 to 2.0 mm.) silica. Boron trifluoride had previously been adsorbed on the silica. The feed to the reactor was 1-decene containing 34.25 percent of a dimer recycle fraction which analyzed about 40 percent 1-decene, 15.4 percent decane and 43.8 percent 20-carbon olefins. The 1-decene feed mixture also contained about 65 ppm. water. This feed mixture was introduced into the reactor at a rate of 75 cc. per hour. About 8.6 cc. (cubic centimeters at standardized conditions of one atmosphere and 15.6° C.) per minute of boron trifluoride were injected into the 1-decene feed line immediately preceding the reactor. The hot spot temperature in the catalyst bed was about 25°–30° C. and the pressure at the reactor outlet was about 100 psig. (0.69 MPa).

EXAMPLE 2

The product stream from the oligomerization reaction described in Example 1 analyzed about 22.3 percent 10-carbon compounds, 20.7 percent 20-carbon compounds, 41.8 percent 30-carbon compounds, 14.2 percent 40-carbon compounds and 1.0 percent 50-carbon and higher compounds. This product stream also contained about 2.77 weight percent of dissolved boron trifluoride. This product stream was directed at a rate of 75 cc. per hour to the top of a one-inch (2.54 cm.) inner diameter glass vacuum column, 22 inches (55.9 cm.) in height and trickled over one-quarter inch (6.4 mm.) Berl saddles, which were packed in the column to a height of 18 inches (45.7 cm.). The temperature in this recovery column, as measured on the external surface, was 23° C. and the pressure of eight inches (203.2 mm.) of mercury was maintained by a vacuum line entering the top of the column through which the boron trifluoride gas was recovered. The liquid product leaving the bottom of the recovery column was analyzed and found to contain 680 ppm. boron trifluoride which is 2.45 percent of the boron trifluoride in the liquid oligomer product entering the recovery column.

EXAMPLE 3

The product stream from the reaction as described in Example 1 was directed to a one-liter glass vessel containing a magnetic stirrer. The feed rate to the vessel was 75 cc. per hour and a draw-off tube was adjusted to maintain an average residence time within the vessel of about 2.5 hours. The liquid temperature was 23° C. and the pressure in the reactor was maintained at about eight inches (203.2 mm.) of mercury. The liquid product removed through the draw-off tube was analyzed and was found to contain 3,400 ppm. of boron trifluoride. This was 12.3 percent of the boron trifluoride content in the liquid oligomer stream entering the recovery vessel. This example demonstrates the incomplete removal of boron trifluoride when the packed column and trickle technique are not used.

It is to be understood that the above disclosure is by way of specific example and that numerous modifications and variations are available to those of ordinary skill in the art without departing from the true spirit and scope of the invention.

We claim:

1. In the oligomerization of a 1-olefin with boron trifluoride catalyst the method for recovering boron trifluoride catalyst that is dissolved in the crude oligomer product mixture resulting from the oligomerization reaction which comprises introducing the crude oligomer product mixture into the top of a non-heated column containing a bed of an inert metallic or ceramic packing material at the temperature of the oligomerization process of between about $-30°$ and about 50° C. and at a maximum pressure of about 600 mm. of Hg. absolute and permitting said oligomer product mixture to trickle through said bed and disperse itself as a thin film on said packing material whereby said boron trifluoride desorbs and vaporizes off and is collected in the pure state for reuse in the oligomerization process and said substantially boron trifluoride-free oligomer product mixture is recovered from the bottom of the column.

2. In the oligomerization of a 1-olefin with boron trifluoride catalyst the method for recovering the boron trifluoride catalyst that is dissolved in the crude oligomer product mixture in accordance with claim 1 in which the 1-olefin comprises 1-decene.

3. In the oligomerization of a 1-olefin with boron trifluoride catalyst the method for recovering the boron trifluoride catalyst that is dissolved in the crude oligomer product mixture in accordance with claim 1 in which the temperature is between about $-10°$ and about 30° C.

4. In the oligomerization of a 1-olefin with boron trifluoride catalyst the method for recovering the boron trifluoride catalyst that is dissolved in the crude oligomer product mixture in accordance with claim 1 in which the recovery is carried out at a maximum pressure in the column of about 300 mm. of Hg. absolute.

5. In the oligomerization of a 1-olefin with boron trifluoride catalyst the method for recovering the boron trifluoride catalyst that is dissolved in the crude oligomer product mixture in accordance with claim 1 in which the liquid hourly space velocity of the oligomer product mixture in the column is between about 0.1 and about 5 hour$^{-1}$.

6. In the oligomerization of a 1-olefin with boron trifluoride catalyst the method for recovering the boron trifluoride catalyst that is dissolved in the crude oligomer product mixture in accordance with claim 1 in which the packing material comprises pieces which are between about 1 and about 50 mm. in their maximum dimension.

* * * * *